United States Patent [19]
Miljkovic et al.

[11] Patent Number: 6,060,465
[45] Date of Patent: May 9, 2000

[54] BILE ACIDS AND THEIR DERIVATIVES AS GLYCOREGULATORY AGENTS

[76] Inventors: Dusan Miljkovic, 4351 Nobel Dr. #62, San Diego, Calif. 92122; Ksenija Kuhajda, Seljačkih buna 77; Momir Mikov, Branimira Ćosića 44, both of 21000 Novi Sad, Yugoslavia; Slavko Kevresan, Veljka Vlahovića 4 21205 Sremski, Karlovci; Ana Sabo, Kulpinska 26, 21470 Bački Petrovac, both of Yugoslavia

[21] Appl. No.: 09/019,330

[22] Filed: Feb. 5, 1998

[30] Foreign Application Priority Data

Feb. 6, 1997 [YU] Yugoslavia .................................. 47/97

[51] Int. Cl.[7] ...................................... A61K 31/56
[52] U.S. Cl. ........................... 514/169; 514/182; 514/866
[58] Field of Search ..................... 514/169, 182, 514/866

[56] References Cited

U.S. PATENT DOCUMENTS 4,337,206  6/1982  Gargani ................................. 260/397.1

OTHER PUBLICATIONS

WPIDS 81–39311D [22], Tokyo Tanabe Co, Sep. 1993.

*Primary Examiner*—Kimberly Jordan
*Attorney, Agent, or Firm*—Robert D. Fish, Esq.; Fish & Associates, LLP

[57] ABSTRACT

Compounds and methods are provided for regulating serum glucose levels in patients by non-parenteral administration of a pharmaceutical in which a primary active ingredient is a cholerically active or other amphiphilic compound. In preferred embodiments the non-parenteral route involves transmucosal administration, and the active substance comprises a salt of a bile acid, bile acid derivative or bile acid analog. In still more preferred embodiments, the transmucosal administration comprises administration to a nasal membrane.

11 Claims, 2 Drawing Sheets

BILE ACIDS AND THEIR DERIVATIVES AS GLYCOREGULATORY AGENTS

FIELD OF THE INVENTION

The present invention relates to the field of cholerically active compounds.

BACKGROUND

Problems relating to the control of serum sugar levels are commonplace in modem industrialized countries. Some diseases relating to sugar levels result from insufficient endogenous insulin, others from so-called insulin insensitivity, and still other conditions from excess levels of insulin. Many of these problems are encompassed within the clinical term, diabetes mellitus, which relates to hyperglycemia, and ranges from late onset forms which can often be controlled by diet and exercise, to forms which are completely dependent on exogenous supplies of insulin or other glucose lowering drugs.

There are numerous known agents for modulating glucose levels in mammals, all of which are generically referred to herein as glycoregulatory compounds, drugs or pharmaceuticals. Among the most widely recognized glycoregulatory compounds are insulin and insulin derivatives, sulphonylurea derivatives, bisguanidine derivatives, reductase inhibitors, K-glucosidase inhibitors, and guar gum. While many of these agents are able to decrease blood glucose levels by at least 20% related to basal levels (Campbell J et al: Acad Press and Royal Society of Medicine, London 1980; McEvoy, American Hospital Pharmacy Association, 1990), only representatives from the first three groups are commonly prescribed. (see, for example, McEvoy: American Hospital Pharmacy Association, 1990, Physician Desk Reference, 1996,; British National Formulary, British Medical Association, London, 1996; Varagic, V., "Farmakologija", Medicinska Knjiga, Beograd, 1996).

One of the greatest problems in treating blood sugar level diseases is not lack of glycoregulatory agents, but administration of such agents. All mammals are thought to regulate blood sugar levels within fairly narrow ranges, and such regulation needs to be almost continuous to adequately compensate for widely varying factors such as intake of sugary foods, and the effects of corticosteroids and other hormones. Continuous, or at least frequent regulation of serum sugar levels presents considerable difficulty from an administration point of view, and many diabetics, for example, find that they need to take insulin on a daily basis. In some instances even daily insulin injections are only partially successful in properly modulating sugar levels, and in any event frequent injections of insulin leads to poor patient compliance. Even where patient complience is satisfactory, a program of frequent injections is extremely undesirable for many reasons, including pain and other effects at the injection sites.

Oral administration of glycoregulatory compounds is known. Unfortunately, all known glycoregulatory agents suffer unacceptable degradation in the gastrointestinal tract, or are problematic for some other reason. (Lee, V. H. L. and Yamamoto, A., Adv. Drug Delivery Rev., 4,171,1990). Absorption across buccal, conjunctival, rectal, vaginal and other mucous membranes are also known as alternative routes to parenteral and oral administration, but the results have generally been unsatisfactory due to poor absorption or local toxicity effects. Insulin is a classic example. Buccal absorption of insulin is minimal in the absence of an absorption enhancing agent, and similar findings have been reported for insulin absorption across the rectal mucosa.

There are several known absorption enhancing agents for trans-mucosal delivery of drugs, including bile acid salts, surfactants, chelating agents, and fatty acid derivatives. Very recently, U.S. Pat. No. 5,661,130 to Meezan et al. (August 1997) suggested the use of nonionic alkyl glycosides as drug absorption enhancing agents.

The use of bile acids and other surfactants to enhance the absorption of peptide drugs (mainly of insulin) started as early as 1932 (Collens, W. S., and Goldzieher, M. A., Proc. Soc. Exp. Biol. Med. 29,756,1932). Bile acid salts are known to improve trans-membrane uptake of endogenous and exogenous lipids in gastrointestinal tract, as well as trans-membrane or para-cell passage of small polar endogenous and exogenous molecules, such as water and inorganic electrolytes (Carey, M. C., in The Liver: Biology and Pathobiology, Eds. Arias, I. M., Popper, H., Schacter, D., Shafritz, D., Raven Press, New York, 1982, p.429), polyethylene glycol (Tagesson, C., and Sjodahl, R., Eur. Surg. Res. 16, 274,1984) and oxalates (Dobbins, J. W., and Binder, H. J., Gastroenterology 70, 1096,1976). The enhancing effect of bile acid salts upon nasal insulin absorption of insulin has been extensively studied in man (Moses, A. C., Gordon, G. S., Carey, M. C., Flier, J. S., Diabetes 32,1040, 1983; Pontiroli, A. E., Alberetto, M., Secchi, A., Dossi, G., Pozza, G., Br. Med. J., 284, 303, 1982; Gordon, G. S., Moses, A. C., Silver, R. D., Flier, J. S. and Carey C. M., Proc. Natl. Acad. Sci. U.S.A. 82, 7419,1985), as well as in other laboratory animals: in rats (Hirai, S., Yashiki, T., Miama, H., Int. J. Pharm 9, 165, 1981; Yamamoto, A., Morita, T., Hashida, M. Sezaki, H., Int. J. Pharm., 93,91, (1993)), and in rabbits Duchateau, G., Zuidema, J., Merkus, F. Int. J. Pharm., 31, 193, 1986; Duchateau, G., Zuidema, J., Basseleur, S., Int. J. Pharm., 39,87,1987; Kubo, H., Hosoya, K., Natsume, H., Sugibayashi, K. Morimoto, Y., Int. J. Pharm., 103,27,1994)).

Many different bile acids have been tested for effectiveness as trans-mucosal absorption enhancers, including deoxycholic acid, cholic acid, taurocholic acid, glycocholic acid, glycodeoxycholic acid, taurodeoxycholic acid, ursodeoxycholic acid and chenodeoxycholic acid. Of these, the most promising effect was found with deoxycholic acid (in nasal insulin absorption), and with cholic acid (in nasal gentamycicn absorption). Even in these instances, however, absorption efficiency is low, and the quantities of bile acids used have been reported to result in unsatisfactory local and systemic toxicity. (Moses et al., Gordon et al., Salzmann et al. and Chadwick, U.S. et al., Gut, 17:10–17 (1976)).

In short, there is still a need to provide new glycoregulatory agents and means of administering such agents.

SUMMARY OF THE INVENTION

In the present invention compounds and methods are provided for regulating serum glucose levels in mammals by non-parenteral administration of a cholerically active compound as an active ingredient.

In preferred embodiments the non-parenteral route involves transmucosal administration, and the active substance comprises a salt of a bile acid, bile acid derivative or bile acid analog. In still more preferred embodiments, the transmucosal administration comprises administration to a nasal membrane.

DETAILED DESCRIPTION

As used herein, the term, "amphiphilic compound" is any compound having a hydrophilic/lipophilic balance (HLB) value between about 2 and about 20, inclusive. Preferred amphiphilic compounds have an HLB value between about 6 and about 16.

As used herein, the term "cholerically active compound" means any amphiphilic compound which (a) comprises a bile acid or salt, (b) structurally resembles a bile acid or salt, (c) specifically reacts with a bile receptor, or (d) has a similar action in the gastrointestinal tract as a bile acid or salt. Included in this definition are all known bile acids, salts, derivatives and analogs thereof, plus structurally similar molecules such as terpenic acids and steroid acids.

As used herein, the term "glycoregulatory pharmaceutical preparation" means a biocompatible formulation intended to regulate a blood (serum) glucose level in a patient.

As used herein, the term "primary active ingredient" in a glycoregulatory pharmaceutical preparation means a compound which is included within the pharmaceutical preparation with the expectation that the ingredient is sufficient by itself to exert a significant glycoregulatory effect. This definition excludes compounds which is included in a pharmaceutical preparation solely or primarily as binders, fillers, preservatives, carriers or as an adjuvant in some other capacity, and specifically excludes compounds which are included in a pharmaceutical preparation solely or primarily to facilitate absorption of another ingredient.

Bile Acids and Related Compounds

Figure 1:
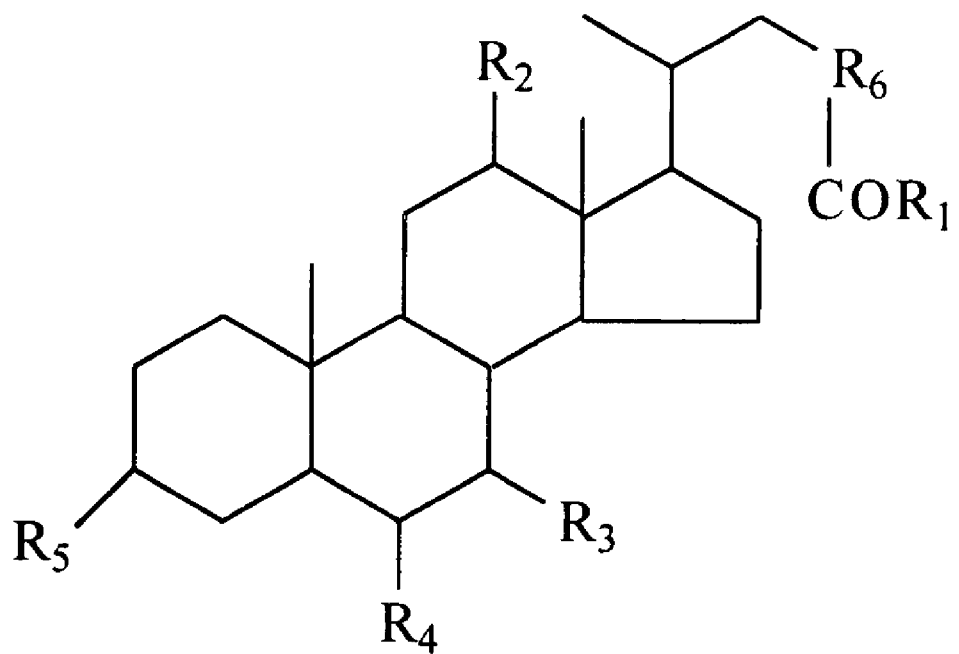
FIG. 1. is a structure exemplifying a class of cholerically active compounds according to the present invention.

There are many known bile acids, including deoxycholic acid, cholic acid, taurocholic acid, glycocholic acid, glycodeoxycholic acid, taurodeoxycholic acid, ursodeoxycholic acid and chenodeoxycholic acid. Each of these compounds can also be functionalized and substituted to encompass a class of compounds, which includes among other things, oxidized and reduced analogs, alkylated and acylated analogs, cyclized or bis-cyclized analogs, and analogs having a shorter or longer side chain. The general structure depicted in FIG. 1 is contemplated to include many of these classes of bile acid related compounds.
wherein:

$R_1$, $R_2$, $R_3$, $R_4$, and $R_5$ are independently hydrogen or XL where

X is nothing, 0, S, NH or NL and L is hydrogen, metallic ion, halogen, an alkyl or alenyl radical having up to 10 carbon atoms, which is branched or unbranched, a cycloalkyl radical having 3 to 8 carbon atoms, or a benzyl radical which is unsubstituted or substituted 1 to 3 times by F, Cl, Br, ($C_1$–$C_4$)-alkyl or ($C_1$–$C_4$)-alkoxy; and where L is bonded to $R_1$, L can alternatively be an amino acid; and $R_6$ is $(CH_2)_n$ where $0 \leq n \leq 5$.

Included in these permutations, it is particularly contemplated that $R_1$ may be amino-, glycine, taurine, alanine or other amino acid group, and $R_2$, $R_3$, $R_4$, and $R_5$ may independently be amino-, hydroxy-, keto- or halogeno-.

One subclass of compounds specifically contemplated to be effective as active glycoregulatory agents are modified bile acids described in U.S. Pat. No. 5,641,767 to Wess et al. (June 1997), the totality of which is incorporated herein by reference. Still another subclass of compounds specifically contemplated to be effective as active glycoregulatory agents are nor- and homo- bile acid derivatives described in U.S. Pat. No. 5,656,277 to Berlati et al. (August 1997), the totality of which is incorporated herein by reference. Still other subclasses of compounds specifically contemplated to be effective as active glycoregulatory agents are the bile acid derivatives described in U.S. Pat. No. 5,610,151 to Glombik et al. (March 1997), the bile acid derivatives described in U.S. Pat. No. 5,428,182 to Enhsen et al. (June 1995), and the cholerically active esters and salts of bile acids described in U.S. Pat. No. 3,910,888 to Widauer et al. (October 1975) all of which are incorporated herein by reference.

Compounds according to the present inventive subject matter are not, however, limited to those falling within the confines of FIG. 1. According to another aspect of the inventive subject matter, an effective compound may include any amphiphilic biological surfactant. Contemplated in this category are terpenic acids and steroid acids.

Administration

It is contemplated that the various cholerically active compounds listed above may be administered transmucosally in any suitable dosage, and according to any suitable regime depending upon the patient's weight, the severity of the symptoms being treated, the amount of compound desired to be absorbed, and the experience and judgment of the prescribing physician. Generally, the appropriate dosage will be that which properly balances the intended results against toxicity and other side effects. Where the condition being treated involves hyperglycemia, for example, an amount is preferred that decreases blood glucose to a normoglycemic or near normoglycemic range. Also preferred is an amount that causes a sustained reduction in blood glucose levels. Even more preferred is an amount sufficient to treat diabetes mellitus by lowering blood glucose level. In such instances satisfactory embodiments would result in at least a 10%, a 20%, a 30% or a 40% reduction in glucose level after one hour compared with controls.

Compounds according to the present inventive subject matter may be provided in virtually any state, including a liquid, e.g. adapted for administration as a spray, a gel, or even a solid, e.g. a powder acceptable for snuffing. Such preparations will usually include ancillary agents, for example a pH-buffering system, preferably a buffer such as phosphate, citrate or acetate buffers, a preservative and an osmotic pressure controlling agent, e.g. glycerol or sodium chloride. Powder formulations may contain in addition to the active agent, an acceptable powdery diluent or mixture thereof, such as cellulose or derivatives thereof, for example cellulose ethers or sodium carboxymethylcellulose, starch, a long chain fatty acid or a salt thereof, e.g. aluminum stearate, an organic polymer, e.g. of an acrylic acid derivative or inorganic vehicles, such as talc or diatomaceous earth. Supplementary addition of water-absorbing polymers, for example polyethylene glycol or polyvinyl pyrrolidone may be desirable to improve adhesion of the powder formulation to the nasal or other mucosa.

Preferred liquid preparations are those in which the diluent is water. Such preparations may be prepared by dispersing the absorption enhancing system in the aqueous medium containing the active agent and ancillary agents, the dispersion being conducted by any method usually employed for suspension or emulsification, e.g. ultrasonic treatment. Adjustment of the aqueous phase to neutrality (i.e. to pH in the range from about 6.5 to about 8) may be accomplished in any of the preparatory steps. Preferably, microemulsions are prepared in which the size of the dispersed particles or droplets is of the order of 10 nm, thereby facilitating their passage across the mucosa. Such microemulsions may be sterilized by filtration. Where a phospholipid or fatty oil is included in the formulations, such additive may advantageously be present in the range of from 0.01 to 10%, preferably from 0.5 to 5% (w/v), and 0.01–50%, preferably from 0.1 to 10% (w/v), respectively, of the preparation. Due to the fact that proteases and peptidases are associated with the nasal mucosa (see R. E. Stratford and V. H. L. Lee: Int. Journ. Pharmaceutics 30 (1986), 73–82) it may be desirable to incorporate biocompatible protease and peptidase inhibitors into polypeptide containing formulations.

The concentration of the active agent in the preparations of this inventive subject matter will of course depend on the particular agent chosen, on its efficacy, on a comparison of its bioavailability by nasal or other transmembranous administration and by other routes of administration, for example parenteral injection, and on the desired frequency of administration combined with the desired single dosage of the formulation. Such pharmacological data can routinely be obtained by the skilled artisan from animal experiments, for example in terms of index values, such as those estimated for insulin preparations in the examples hereinafter provided. Referring now to numerical quantities, especially preferred embodiments may involve an intranasal daily dosage within the range of about 2 mg/kg of body mass, which equates to about 140 mg/day for a 70 kg man. Preferred concentrations of active ingredient in such dosing are contemplated to be about 0.5 gm % to about 5 gm %, and viewed from another aspect it is contemplated that a 1% solution of active ingredient may be administered in a dose equaling about 20 $\mu$L per 100 gm of body weight.

Transmucosal absorption of cholerically active compounds is contemplated to be very rapid, with about 50% of the compound being absorbed within 30 minutes. The rate can be altered somewhat according to the distribution of the active substance across the membrane involved, and of course, according to the particular membrane involved. For intranasal delivery, for example, a spray may be more desirable than a dropper or cotton swab. Aerosols and suppositories are also contemplated.

Sustained release formulations are also contemplated. The sustained release format can be an ocular insert, erodible microparticulates, swelling mucoadhesive particulates, pH sensitive microparticulates, nanoparticles/latex systems, ion-exchange resins and other polymeric gels and implants (Ocusert, Alza Corp., California Joshi, A., S. Ping and K. J. Himmelstein, Patent Application WO 91/19481). These systems maintain prolonged drug contact with the absorptive surface preventing washout and nonproductive drug loss.

The preparations of this inventive subject matter may be used in any dosage dispensing device adapted for transmucosal administration. Such devices may advantageously be constructed with a view to ascertaining optimum metering accuracy and compatibility of its constructive elements, such as container, valve and actuator for use with nasal formulations, and could be based on a mechanical pump system, e.g. that of a metered-dose nebulizer, or on a pressurized aerosol system. The aerosol system requires the propellant to be inert towards the formulation. Suitable propellants may be selected among such gases as fluorocarbons, hydrocarbons, nitrogen and dinitrogen oxide or mixtures thereof.

It is contemplated that any suitable membrane can be used to receive a cholerically active compound to modulate blood sugar levels. In addition to nasal membranes, for example, compounds according to the present inventive subject matter can be applied rectally, vaginally, orally, (sublingually or bucally), conjunctally, or by inhalation. It is also contemplated that compounds according to the present inventive subject matter can even be effective when absorbed through the mucous membranes of the digestive tract.

Synthesis

Compounds according to the present inventive subject matter can be readily synthesized according to known chemistry. In several instances, such as deoxycholic acid, cholic acid, taurocholic acid, glycocholic acid, glycodeoxycholic acid, taurodeoxycholic acid, ursodeoxycholic acid and chenodeoxycholic acid, the compounds are commercially available in purified forms. In other instances, such as the various modified bile acids and analogs thereof discussed above, the compounds can be synthesized according to procedures set forth or readily derivable from the various identified patents.

Further details of practicing this inventive subject matter are furnished by way of the following examples which, however, should not be construed so as to imposes any kind of limitation to the scope of the invention.

EXAMPLES

The Na salt of 3K7K-12-keto-5-2-cholanic acid (as a 0.8% physiological solution) was prepared according to known procedures analogous to those set forth in D. A. Miljkovic, K. N. Kuhaja, J. T. Hranisavljevic, "A rational synthesis of 3-mono-acyl derivatives of deoxycholic acid", *Review of Research, Faculty of Sciences, Novi Sad*, 12, 39 (1982), and D. A. Miljkovic, J. J. Csanadi, J. A. Petrovic, J. T. Hranisavljevic, "Synthesis and chromatographic separation of some 12-doxy-12-halogeno-derivatives of cholic acid", *Review of Research, Faculty of Sciences, Novi Sad*, 12, 45 (1982). The solution was adjusted to pH 7.4 by addition of diluted HCl (0.1 molar), and administered upon the nasal mucosa of laboratory rats by dropping pipette. The lowest glucose blood level was reached approximately one hour after administration, after which the glucose level rose mildly until the end of the second hour, and then remained approximately stable during the following four hours.

Table 1 lists data from a comparative study of lowering of the blood glucose concentration after nasal administration of insulin, Na-salt of 3K,7K-dihydroxy,12-keto-52-cholanic acid (0.8%), a mixture of insulin and Na-salt of 3K,7K-dihydroxy,12-keto-52-cholanic acid, as well as after a subcutaneous administration of insulin. The time dependent decrease of the glucose level was calculated on the basis of the area under the obtained curves of FIG. 2.

TABLE 1

| Decrease of glucose after nasal administration of bellow given substances in physiological solution (0.8% active substance) | % Glucose decrease |
| --- | --- |
| Nasal administration of insulin | 4.0 |
| Nasal administration of Na-salt of 3K,7K-dihydroxy-52-cholanic acid | 12.9 |
| Nasal admimstration of insulin and Na-salt of the above acid | 19.3 |
| Insulin - subcutaneously | 36 |

As expected, the most pronounced glucose concentration decrease in the rat blood was achieved upon subcutaneous insulin administration, while the least effect was observed with nasally applied insulin (alone, without any promoters). With a nasal administration of a mixture of insulin and Na-salt of 3K,7K-hydroxy,12-keto-52-cholanic acid, glu cose concentration decrease reached 54% of the decrease obtained with subcutaneous injection of insulin. Significantly, after a nasal administration of a 0.8% Na-salt of 3K,7K-dihydroxy,12keto-52-cholanic acid in physiological solution, the glucose concentration reached about 36% less than that obtained with subcutaneous insulin administration.

Figure 2:
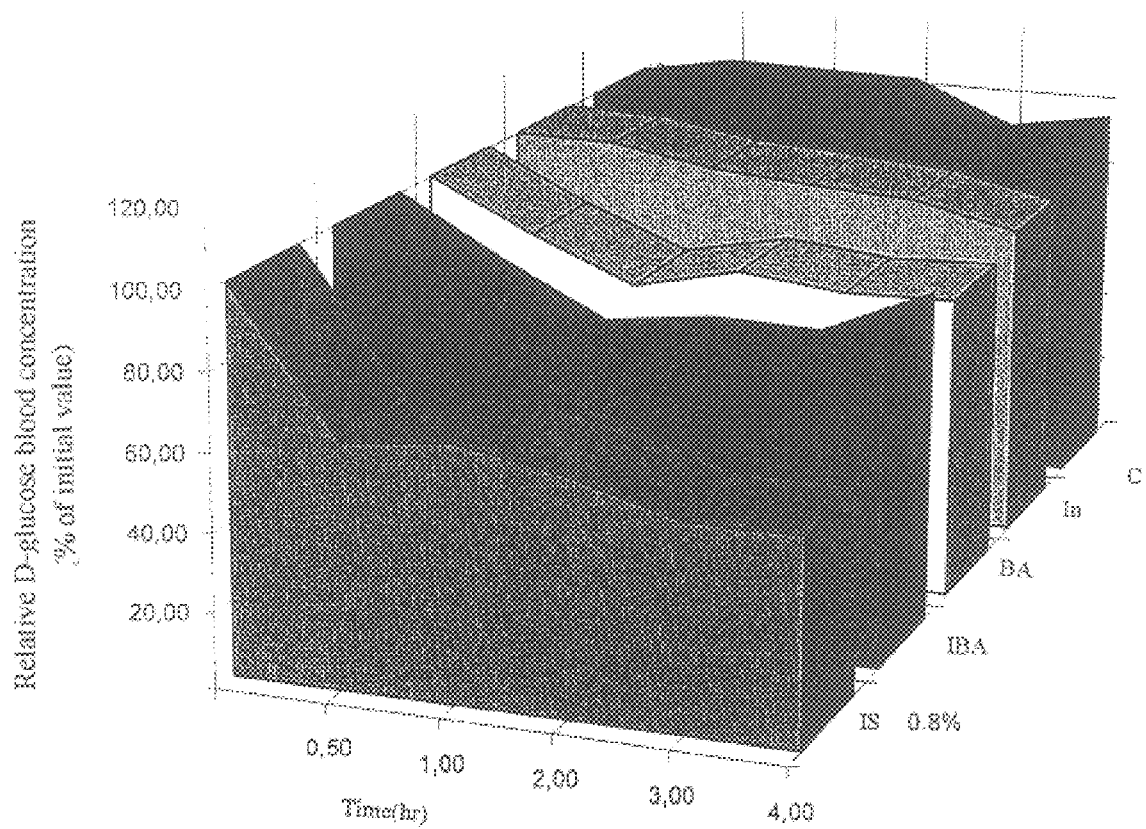
FIG. 2. is a graph showing the effect of nasal application of a compound according to the present invention.

FIG. 2 is a graph showing the relative effectiveness on rat blood sugar levels over a four hour period of nasal applications of the following compositions: a physiological solution ( C ), an insulin solution (In), a solution of Na-salt of 3K,7K-dihydroxy,12-keto-5-2-cholanic acid (BA), a solution of a mixture of insulin and Na salt of 3K,7K-dihydroxy, 12-keto-5-2-cholanic acid (IBA), as well as a subcutaneous application of insulin (IS). In FIG. 2, the median blood glucose concentration values are given; the number of animals per group was 5. Insulin was applied at 10U/kg in both nasal and subcutaneous mode. Bile acid salt was in 0.8% concentration. The glucose level was followed with an Accutrend mini, Boehringer, Manheim.

Without limiting the validity of the appended claims by any particular theory or mechanism of action, the present applicants consider that the above-described results can reasonably be extrapolated to generalize glycoregulatory effects of transmucosal administration of bile acids, their natural or synthetic derivatives, analogs and homologs, per se, across many species. Such extrapolation is based in part on the recognition that bile acids and salts appear to have specific membranous receptor sites, and in part on the recognition that the structure of bile acids is extremely conservative over a very large number of species spanning millions of years of evolution (see e.g., Michel W. C., "Evidence of distinct amino acid and bile salt receptors in the olfactory system of the zebrafish, Danio rerio", *Brain Res.*, 764(1–2), 179–87 (1997); Li, W. et al., "The olfactory system of migratory adult sea lamprey (Petromyzon marinus) is specifically and acutely sensitive to unique bile acids released by conspecific larvae", *J. Gen. Physiol.*, 105(5), 569–87 (1995); Lo, Y. H., et al., "Signal transduction for taurocholic acid in the olfactory system of Atlantic salmon", *Chem Senses*, 19(5), 371–80 (1994)). Still another basis for the extrapolation is that the effects of bile acids and salts appear to affect synthesis down to the very basic gene level in both rats and humans. (see e.g., Chiang, J. Y and Stroup D., "Identification and characterization of a putative bile acid-responsive element in cholesterol 7 alpha-hydroxylse gene promoter", *J. Biol. Chem.*, 269(26), 17502–7 (1994)). It is thus contemplated that bile acids, their natural or synthetic derivatives, analogs and homologs are effective even without insulin or any other agent to decrease concentration of D-glucose in the blood of many animals, including mammals. The results set forth herein also demonstrate that certain semysinthetic derivatives, such as 12-dehydrocholic acid, improve insulin absorption to a greater extent than other bile-like compounds previously described for this purpose.

Thus, amphiphilic, and especially cholerically active compounds, have been disclosed to be effective as primary active ingredients in glycoregulatory pharmaceutical preparations. Therefore, while specific embodiments have been disclosed herein, the scope of the invention is not be limited except through interpretation of the appended claims.

We claim:

1. A method of treating hyperglycemia comprising:
   identifying an amphiphilic active compound as effective to lower a blood sugar level in a patient by at least 10% within 1 hour after administration relative to a control;
   providing the compound as a primary active ingredient in a glycoregulatory pharmaceutical preparation;
   intranasally administering the pharmaceutical preparation.

2. The method of claim 1 wherein the amphiphilic compound comprises a cholerically active compound.

3. The method of claim 1 wherein the amphiphilic compound comprises a pharmaceutically acceptable form of a bile acid, bile acid derivative or bile acid analog.

4. The method of claim 1 wherein the amphiphilic compound is given by the formula:

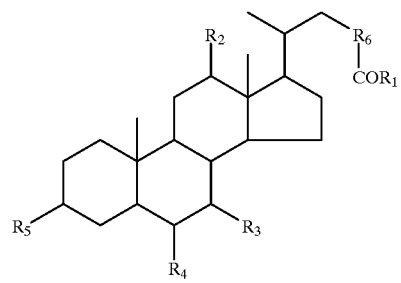

wherein:

$R_1$, $R_2$, $R_3$, $R_4$, and $R_5$ are independently hydrogen or XL where

X is nothing, O, S, NH or NL and L is hydrogen, metallic ion, an alkyl or alkenyl radical having up to 10 carbon atoms, which is branched or unbranched, a cycloalkyl radical having 3 to 8 carbon atoms, or a benzyl radical which is unsubstituted or substituted 1 to 3 times by F, Cl, Br, $(C_1-C_4)$-alkyl or $(C_1-C_4)$-alkoxy; and where L is bonded to $R_1$, L can alternatively be an amino acid; and $R_6$ is $(CH_2)_n$ where $0 \leq n \leq 5$.

5. The method of claim 2 wherein the cholerically active compound is selected from the group consisting of deoxycholic acid, cholic acid, taurocholic acid, glycocholic acid, glycodeoxycholic acid, taurodeoxycholic acid, ursodeoxycholic acid and chenodeoxycholic acid.

6. The method of claim 2 wherein the cholerically active compound comprises 3K,7K-dihydroxy-12-keto-5-2-cholanic acid.

7. The method of claim 1 wherein the amphiphilic compound has a hydrophilic/lipophilic balance (HLB) value between about 2 and about 20, inclusive.

8. The method of claim 1 wherein the amphiphilic compound has a hydrophilic/lipophilic balance (HLB) value between about 6 and about 16.

9. The method of any of claims 1–8 further comprising employing the pharmaceutical preparation to lower the blood sugar level in the patient by at least 20% within 1 hour after administration relative to the control.

10. The method of any of claims 1–8 further comprising employing the pharmaceutical preparation to lower the blood sugar level in the patient by at least 30% within 1 hour after administration relative to the control.

11. The method of any of claims 1–8 further comprising employing the pharmaceutical preparation to lower the blood sugar level in the patient by at least 40% within 1 hour after administration relative to the control.

* * * * *